(12) United States Patent
Maguire et al.

(10) Patent No.: US 9,743,875 B2
(45) Date of Patent: Aug. 29, 2017

(54) AUTOMATED VESSEL PUNCTURE DEVICE USING THREE-DIMENSIONAL(3D) NEAR INFRARED (NIR) IMAGING AND A ROBOTICALLY DRIVEN NEEDLE

(71) Applicant: VascuLogic, LLC, Piscataway, NJ (US)

(72) Inventors: Tim Maguire, Piscataway, NJ (US); Kevin Nikitczuk, North Brunswick, NJ (US); Martin Yarmush, Newton, MA (US); Eric Novik, Edison, NJ (US); Stanley Dunn, Troy, NY (US)

(73) Assignee: VascuLogic, LLC, Piscataway, NJ (US)

( * ) Notice: Subject to any disclaimer, the term of this patent is extended or adjusted under 35 U.S.C. 154(b) by 0 days.

(21) Appl. No.: 14/851,885

(22) Filed: Sep. 11, 2015

(65) Prior Publication Data

US 2015/0374273 A1    Dec. 31, 2015

Related U.S. Application Data

(63) Continuation-in-part of application No. 13/124,324, filed as application No. PCT/US2009/062550 on Oct. 29, 2009, now abandoned.

(Continued)

(51) Int. Cl.
| | |
|---|---|
| A61B 5/15 | (2006.01) |
| A61B 5/00 | (2006.01) |
| A61B 17/34 | (2006.01) |
| A61M 5/32 | (2006.01) |
| A61M 5/42 | (2006.01) |
| A61B 90/13 | (2016.01) |

(Continued)

(52) U.S. Cl.
CPC ...... *A61B 5/150748* (2013.01); *A61B 5/0059* (2013.01); *A61B 5/489* (2013.01); *A61B 17/3403* (2013.01); *A61B 34/30* (2016.02); *A61B 34/76* (2016.02); *A61B 90/13* (2016.02); *A61M 5/3287* (2013.01); *A61M 5/427* (2013.01); *A61B 2017/3407* (2013.01); *A61B 2017/3409* (2013.01); *A61B 2034/105* (2016.02); *A61B 2034/2059* (2016.02); *A61B 2090/373* (2016.02)

(58) Field of Classification Search
CPC ............ A61B 17/3403; A61B 19/2203; A61B 2017/3403–2017/3409; A61B 2019/2292; A61B 2019/505
See application file for complete search history.

(56) References Cited

U.S. PATENT DOCUMENTS 5,078,140 A    1/1992  Kwoh
5,368,574 A *  11/1994  Antonacci ......... A61M 25/0662
                                                    604/167.02

(Continued)

OTHER PUBLICATIONS

International Search Report and Written Opinion issued in connection with corresponding International Application No. PCT/US2009/062550.

*Primary Examiner* — Michael C Stout
(74) *Attorney, Agent, or Firm* — Davidson, Davidson & Kappel, LLC

(57) ABSTRACT

The present invention is directed to an automated vessel puncture device, methods of mapping three-dimensional views of subcutaneous vessels and methods for providing simultaneous real-time diagnostic assay.

20 Claims, 9 Drawing Sheets

Related U.S. Application Data

(60) Provisional application No. 61/109,394, filed on Oct. 29, 2008.

(51) Int. Cl.
*A61B 34/30* (2016.01)
*A61B 34/00* (2016.01)
A61B 90/00 (2016.01)
A61B 34/10 (2016.01)
A61B 34/20 (2016.01)

(56) References Cited

U.S. PATENT DOCUMENTS

| | | | |
|---|---|---|---|
| 5,479,969 A | 1/1996 | Hardie et al. | |
| 5,584,850 A * | 12/1996 | Hart | A61B 17/3498 604/278 |
| 5,718,237 A * | 2/1998 | Haaga | A61B 10/0275 128/DIG. 8 |
| 5,752,938 A * | 5/1998 | Flatland | A61B 17/3462 604/167.01 |
| 5,813,988 A * | 9/1998 | Alfano | A61B 5/0073 356/432 |
| 5,954,701 A * | 9/1999 | Matalon | A61M 25/0693 604/272 |
| 5,995,866 A * | 11/1999 | Lemelson | A61B 18/20 250/461.2 |
| 6,033,369 A * | 3/2000 | Goldenberg | A61B 10/025 600/567 |
| 6,142,980 A * | 11/2000 | Schalk | A61M 1/0031 137/512.3 |
| 6,162,203 A * | 12/2000 | Haaga | A61B 10/0275 128/898 |
| 6,200,262 B1 * | 3/2001 | Ouchi | A61B 1/00137 600/154 |
| 6,221,029 B1 * | 4/2001 | Mathis | A61B 10/0233 600/564 |
| 6,273,861 B1 * | 8/2001 | Bates | A61B 10/0275 600/567 |
| 6,290,476 B1 * | 9/2001 | Wu | F04B 33/005 417/549 |
| 6,375,627 B1 * | 4/2002 | Mauze | A61B 5/1411 600/309 |
| 6,409,967 B1 * | 6/2002 | McIntosh | A61M 1/3627 137/238 |
| 6,419,278 B1 * | 7/2002 | Cunningham | F16L 33/2071 285/256 |
| 6,439,541 B1 * | 8/2002 | Nosel | 606/139 |
| 6,463,309 B1 * | 10/2002 | Ilia | A61B 5/0059 382/128 |
| 6,514,215 B1 * | 2/2003 | Ouchi | A61B 17/3498 251/149.1 |
| 6,652,461 B1 * | 11/2003 | Levkovitz | A61B 8/04 128/916 |
| 7,225,005 B2 | 5/2007 | Kaufman et al. | |
| 7,627,365 B2 * | 12/2009 | Chance | A61B 5/0073 600/323 |
| 7,792,334 B2 | 9/2010 | Cohen et al. | |
| 8,231,525 B2 * | 7/2012 | Cohen | A61B 1/00137 600/154 |
| 2002/0111634 A1 * | 8/2002 | Stoianovici | A61B 90/50 606/129 |
| 2002/0143293 A1 * | 10/2002 | Francavilla | A61B 5/1405 604/116 |
| 2002/0168618 A1 | 11/2002 | Anderson et al. | |
| 2003/0088153 A1 * | 5/2003 | Carrillo, Jr. | A61M 25/0606 604/506 |
| 2003/0093058 A1 * | 5/2003 | Siang Teo | A61B 1/015 600/564 |
| 2003/0199753 A1 * | 10/2003 | Hibner | A61M 25/0075 600/114 |
| 2004/0002632 A1 * | 1/2004 | D'Arrigo | A61B 10/0283 600/411 |
| 2004/0010230 A1 * | 1/2004 | Dittrich | A61B 17/0206 600/210 |
| 2004/0060563 A1 * | 4/2004 | Rapacki | A61B 17/3462 604/167.06 |
| 2005/0043682 A1 * | 2/2005 | Kucklick | A61B 17/12022 128/207.14 |
| 2005/0096605 A1 * | 5/2005 | Green | A61B 17/3498 604/167.03 |
| 2005/0113757 A1 * | 5/2005 | McFarlane | A61B 17/3421 604/164.09 |
| 2005/0131349 A1 * | 6/2005 | Albrecht | A61M 39/06 604/246 |
| 2005/0165356 A1 * | 7/2005 | Pasqualucci | A61B 17/3462 604/167.06 |
| 2005/0168980 A1 * | 8/2005 | Dryden | A61B 5/489 362/230 |
| 2005/0177201 A1 * | 8/2005 | Freeman | A61N 1/0529 607/46 |
| 2005/0228291 A1 * | 10/2005 | Chance | A61B 5/0073 600/476 |
| 2005/0287072 A1 * | 12/2005 | Contag | A01K 67/0275 424/9.6 |
| 2006/0020279 A1 * | 1/2006 | Chauhan | A61B 90/36 606/167 |
| 2006/0129037 A1 * | 6/2006 | Kaufman | A61B 5/14535 600/322 |
| 2006/0129038 A1 * | 6/2006 | Zelenchuk | A61B 5/14535 600/322 |
| 2006/0173351 A1 * | 8/2006 | Marcotte | A61B 5/0059 600/473 |
| 2006/0229531 A1 * | 10/2006 | Goldberger | A61B 5/1427 600/573 |
| 2006/0293643 A1 * | 12/2006 | Wallace | A61B 34/20 606/1 |
| 2007/0040907 A1 * | 2/2007 | Kern | A61B 5/0059 348/77 |
| 2007/0073156 A1 * | 3/2007 | Zilberman | A61B 5/0064 600/473 |
| 2007/0206099 A1 * | 9/2007 | Matsuo | G06K 9/00033 348/208.12 |
| 2007/0253607 A1 * | 11/2007 | Higuchi | G06K 9/00026 382/124 |
| 2008/0027317 A1 * | 1/2008 | Wood | A61B 5/0059 600/427 |
| 2008/0137926 A1 * | 6/2008 | Skinner | G06K 9/34 382/131 |
| 2008/0146915 A1 * | 6/2008 | McMorrow | A61B 5/1422 600/424 |
| 2008/0195043 A1 * | 8/2008 | Schwach | A61B 5/0059 604/116 |
| 2008/0200820 A1 | 8/2008 | Amitzur et al. | |
| 2008/0275396 A1 * | 11/2008 | Neerken | A61B 5/0059 604/116 |
| 2008/0306392 A1 * | 12/2008 | Satoguchi | A61B 5/0059 600/479 |
| 2009/0021739 A1 * | 1/2009 | Tsujita | A61B 1/00163 356/407 |
| 2009/0118670 A1 * | 5/2009 | Neerken | A61B 5/0059 604/116 |
| 2009/0149867 A1 * | 6/2009 | Glozman | A61B 17/3478 606/130 |
| 2009/0245601 A1 * | 10/2009 | Cohen | A61B 5/489 382/128 |
| 2009/0248038 A1 * | 10/2009 | Blumenkranz | B25J 13/085 606/130 |
| 2009/0248041 A1 * | 10/2009 | Williams | A61B 8/12 606/130 |
| 2009/0275823 A1 * | 11/2009 | Ayati | A61B 5/1411 600/424 |
| 2010/0010505 A1 * | 1/2010 | Herlihy | A61B 90/11 606/130 |
| 2010/0160752 A1 | 6/2010 | Chance | |
| 2010/0172567 A1 * | 7/2010 | Prokoski | A61B 5/0064 382/132 |

(56) References Cited

U.S. PATENT DOCUMENTS

2010/0174160 A1   7/2010  Chance
2012/0190981 A1   7/2012  Harris et al.
2015/0065916 A1   3/2015  Maguire et al.

* cited by examiner

Circle = light source (LED)
Square = photodetector

AUTOMATED VESSEL PUNCTURE DEVICE USING THREE-DIMENSIONAL(3D) NEAR INFRARED (NIR) IMAGING AND A ROBOTICALLY DRIVEN NEEDLE

This application is a continuation application of U.S. application Ser. No. 13/124,324, filed on Aug. 19, 2011, which is a national stage application of International Application No. PCT/US2009/062550, filed on Oct. 29, 2009, which claims priority to U.S. Provisional Application No. 61/109,394, filed on Oct. 29, 2008, the disclosures of which are all hereby incorporated by reference herein.

BACKGROUND OF THE INVENTION

Venipuncture is the process of obtaining a sample of venous blood for purposes of performing various tests. Most samples are commonly obtained from a vein or organ that lies close to the surface of the skin. For example, usually the median cubital vein on the anterior forearm for venipunture.

Currently, venipunctures are executed manually by trained personnel, but there are problems inherent with these processes. Many times locating a vein is a challenge, especially in younger and elderly individuals. To complicate matters, multiple attempts at needle insertion may be required, due either to the inexperience of the person obtaining the sample, and/or from difficulty in locating the target vein, resulting in discomfort to the patient and bruising.

It was first demonstrated in the 1930s that infrared light can be used to image subcutaneous veins, based on the principle that near infrared (NIR) light has the ability to penetrate human tissue better than visible light and is differentially absorbed by oxygenated and deoxygenated hemoglobin. Skin and some other body tissues reflect infrared light in the near-infrared wavelength range of about 700 to 900 nanometers, while blood absorbs radiation in this range. Thus, in video images of body tissue taken under infrared illumination, vessels, e.g. blood vessel or organs, appear as dark lines against a lighter background of surrounding fatty tissue. Therefore, a target vessel can be "illuminated" by finding the positions where the light absorption difference between deoxyhemoglobin and oxyhemoglobin is the greatest.

To aid in locating target veins for venipunture, some companies have commercialized systems using imaging techniques—one example is Lumintex's VeinViewer. This device detects subcutaneous veins and projects a real time image back on the skin, providing a two-dimensional (2D) positional guide for venipuncture. Although this technology may provide methods of viewing veins externally, it does not provide any depth representation of the veins under the skin, leaving the question of how far and deep to insert the needle to a human estimation. The actual venipuncture must therefore be performed manually, leading to the inevitable human error.

Some ongoing studies have resulted in a pseudo three-dimensional (3D) imaging systems to serve as the guidance for an automatic catheterization device. These methods use near infrared (NIR) imaging to localize and map superficial veins and a separate NIR based laser system to generate a 3D topological map of the skin surface. Two-dimensional (2D) masks of the vessels are generated and then projected onto the 3D topological maps. In this system, only an estimation of actual vessel position is generated, because no measurements of vessel depth from the surface of the skin are ever computed. Therefore, when attempting to guide the needle into the vein, there is no accurate value as to how deep to drive the needle.

There is also broad research being performed that will robotically guide a needle. One company, ImageGuide, Inc. (part of GE Medical Systems), uses this technology in conjunction with current commercial imaging systems such as CT and MR. These methods, however, use cumbersome and non-portable devices for both the viewing and robotics. Currently, there is no commercial technology that combines an imaging system with a robotically driven needle in a portable unit for the purpose of venipuncture.

OBJECTS AND SUMMARY OF THE INVENTION

It is an object of the present invention to provide a self-contained, compact, portable device for autonomous venipuncture.

It is another object of the present invention to provide a compact, portable device that will non-invasively image and map in real time the three-dimensional (3D) spatial coordinates of subcutaneous vessels in order to robotically direct a needle into the optimal or designated vessel for a puncture.

It is another object of the present invention to provide a compact, portable device adaptable for receiving feedback from pressure and visual sensors which aid in the puncture process.

It is yet another embodiment to provide a self-contained, compact, portable device for vessel puncture.

It is another object of the present invention to provide a method for venipuncture utilizing a compact, portable puncture device.

It is yet another object of the present invention to provide an all-in-one point of care device for venipuncture and for providing simultaneous real-time diagnostic assays.

It is an object of the present invention to provide methods for obtaining analytical assays such as glucose monitoring, pregnancy/ovulation testing, coagulation/PT evaluation, fecal occult blood, determination of drugs of abuse, detection of bacterial infections (e.g., *H. pylori*), detection of HIV, and monitoring of cholesterol levels utilizing the automated venipuncture device.

In accordance with the above-mentioned objects, the present invention is directed to an, automated venipuncture device containing three major components: (1) an imaging system; (2) an automated robotic end-effector unit; and (3) a computer (controller and interface).

In certain preferred embodiments, the portable automated venipuncture device is adapted for placement on an appendage of a human, an comprises: i) a near infrared three-dimensional imaging system for illuminating a target vein for venipuncture comprising at least one infrared light source for emitting infrared light and at least one light detector for capturing reflected near infrared light from the target vein; ii) an automated robotic end-effector unit comprising a needle for target vein puncture and a needle guidance system that utilizes haptic and force feedback profiles for positioning the needle at the target vessel; and iii) a computer connected to the imaging system and end-effector unit, said computer receiving information from the imaging system and end-effector unit and generating haptic force and feedback profiles to position the needle and adjust the amount of force applied to the needle to puncture the target vessel of a human, such that when the imaging system and the end-effector unit are attached to an appendage of a human a three-dimensional map of subcutaneous vessel is generated and an optimal vessel is targeted for venipuncture.

In certain preferred embodiments, the automated venipuncture device is a self-contained device.

Using near-infrared (NIR) imaging techniques, subcutaneous veins can be imaged and a three-dimensional map of major superficial vessels constructed on a computer. Using both instant and real time coordinates generated by the imaging system and haptic feedback from the automated robotic end-effector unit, the robotically controlled needle can be guided into a target vessel.

The imaging system and end-effector unit can be contained in a single unit. This unit will be capable of either being mounted onto a target limb (classically the forearm for venipunture) of the subject or the target limb will be placed onto a stationary unit (e.g., a table). The imaging system and end-effector unit can be remotely connected to a computer which controls the image processing and robotic automation.

In certain other embodiments, the present invention is directed to a method of mapping a three-dimensional view of subcutaneous veins for automated venipuncture utilizing an automated venipuncture device, wherein the method has the following steps: i) attaching the portable automated venipuncture device on an appendage of a human; ii) capturing still images of subcutaneous vessels on a computer generated from the near infrared three-dimensional imaging system of the automated venipuncture device; iii) creating an image threshold using profiles of pixel intensity values of the still images, and refining contrast and clarity of the image; iv) conducting segment surface extraction and smoothing to define boarders and midline of subcutaneous vessels; v) conducting mesh generation to define a default three-dimensional geometry representing size and shape of the subcutaneous vessels; vi) optimizing the mesh generation using segmented images to generate a true three-dimensional representation of the subcutaneous vessels; and vii) obtaining a final three-dimensional volumetric reconstruction of the subcutaneous veins.

In certain other embodiments, the present invention is further directed to a method of controlling needle positioning of an automated venipuncture device of the present invention, wherein the method has the following steps: i) calculating a relative target position of the needle tip utilizing a three-dimensional volumetric reconstruction of subcutaneous vessels; ii) calculating a reference distance of the needle tip utilizing a position sensor located on the imaging system; iii) calculating the absolute target position of the needle tip based on the relative target position of step i) that is adjusted based on the reference distance of step ii); iv) tracking the displacement of the needle device carrier by the position sensor; v) evaluating the displacement of the needle verses the absolute target position utilizing a feedback loop within the automated venipuncture device, wherein needle placement is stopped when the needle displacement and absolute target position coincide; and vi) ensuring the correct angle of injection utilizing fine motor positioning adjustments, such that venipuncture to an optimal vein is provided.

The present invention is also directed to an all-in-one point of care device by coupling the automated venipuncture device of the present invention with real-time diagnostic assays.

In certain embodiments, the present invention is further directed to method for providing simultaneous real-time diagnostic assays by: i) obtaining a blood sample utilizing the self contained, automated venipuncture device of claim 1; and ii) simultaneously introducing said blood sample into a point of care diagnostic assay.

The creation of three-dimensional (3D) coordinate representation of superficial vessels in a rapid and real time manner eliminates any guess work and allows precise needle insertion. The automated venipuncture device of the present invention therefore eliminates human error and potential multiple and incorrect punctures that are common occurrences when performing a venipuncture, each of which can cause trauma and painful bruising for the human.

The methods utilized in the present invention can increase patient comfort, provide for rapid phlebotomy and increase the overall efficiency for extremely common procedures, all of which are priority in health care.

DETAILED DESCRIPTION OF THE INVENTION

The self-contained, automated venipuncture device of the present invention provides a fully automated puncture device that combines novel near infrared (NIR) imaging techniques to generate a three-dimensional (3D) map of subcutaneous vessels in real time, combined with a computer-controlled, automated robotic end-effector unit that allows for portable application essentially anywhere.

The self-contained, automated venipuncture device is comprised of three major components: i) a three-dimensional (3D) vessel imaging system; ii) an automated robotic end-effector unit; and iii) a computer.

Subcutaneous Vessel Imaging System

In order to "illuminate" a target vessel, the automated venipuncture device of the present invention contains a three-dimensional (3D) imaging system that non-invasively maps the target veins, for example a subcutaneous network of blood vessels.

The three-dimensional (3D) imaging system of the present invention contains a light source for emitting infrared light and light detectors for capturing reflected near infrared light. In certain embodiments of the present invention, the light source may be a single or a plurality of light emitting diodes (LEDs) that provide infrared light to target veins from different illumination directions.

Figure 7:
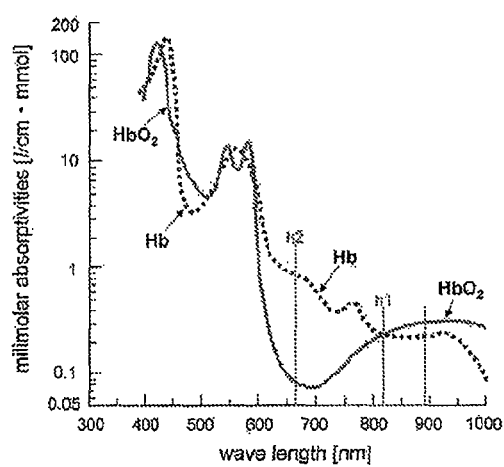
FIG. 7 is a graph showing the wavelength absorptivities of deoxy-HB and oxy-Hb.

The light emitting diodes (LEDs) utilized in the imaging system preferably have a wavelength ranging from about 730 nm to about 910 nm. In certain preferred embodiments, the light emitting diodes have a wavelength ranging from about 730 nm to about 850 nm; 730 nm being near the peak absorption of deoxy-Hb and 850 nm being near the peak absorption of oxy-Hb and just beyond the minimum absorption of deoxy-Hb (See: FIG. 7).

Light emitting diodes (LEDs) of other frequencies are also contemplated for use in the imaging system of the present invention.

In certain other embodiments, the present invention may utilize other sources of light.

The imaging system of the automated venipuncture device of the present invention also preferably contains a single or a plurality of light detectors. In certain preferred embodiments, the light detectors are photodetectors. Photodetectors are the preferred light detector for image capture because of their relatively lower costs over other light detectors.

Figure 8:
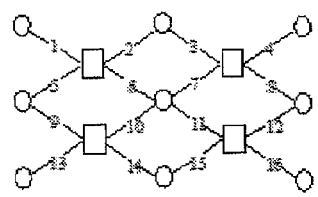
FIG. 8 is a diagram showing one possible configuration of light emitting diodes and light detectors of the imaging system.

In certain embodiments of the present invention, the near infrared light emitting diodes are arranged in an array that preferably also includes the photodetectors. One possible configuration is as shown in FIG. 8, wherein the circles represent the LEDs and the squares represent the photodetector.

In this embodiment, there are nine (9) light emitting diodes, each capable of generating light at either 700 nm or 910 nm, and four (4) photodetectors, resulting in 16 possible LED-detector pairings, each corresponding to a possible orientation of the subcutaneous vessels. The raw measurement from the imaging system is:

$$D=(f_{deoxy,1}-f_{oxy,1})-(f_{deoxy,2}-f_{oxy,2})$$

where 1 and 2 refer to two different LEDs. The quantity D is a vector, having a magnitude representing the difference of differential absorption and a direction representing any two of the paths enumerated above. This particular embodiment is not intended to be limiting in any way.

During the imaging process, the $D_i$ measurements are collected and then used to reconstruct the position and orientation of the subcutaneous vein. Back-projection techniques similar to traditional computed tomography are then used to compute the 3D reconstruction. With this data, a 3D coordinate system can be generated that will be used to automatically guide the robotically driven needle.

In certain other embodiments, near infrared sensitive charged-coupled device (CCD) cameras may be used to detect reflected light, in combination with specific filters to enhance the signal.

Figure 2A:
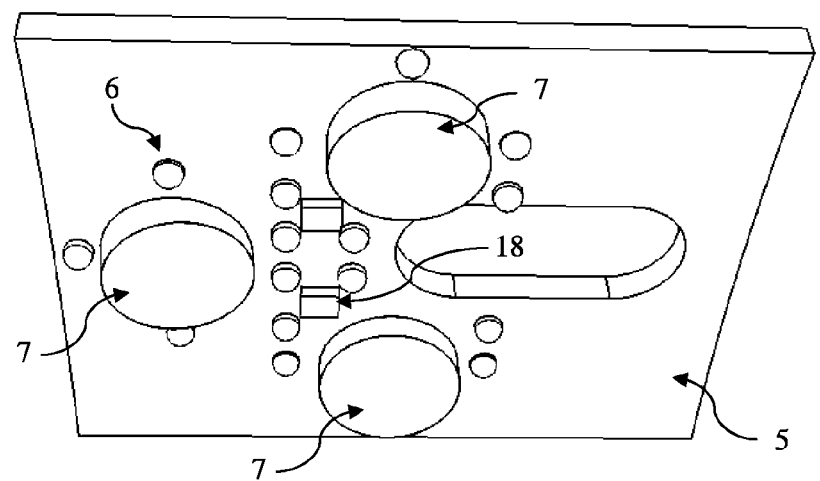
FIGS. 2A and 2B illustrate an underside layout of an imaging system housing plate and the assembly of imaging system components.
Figure 2B:
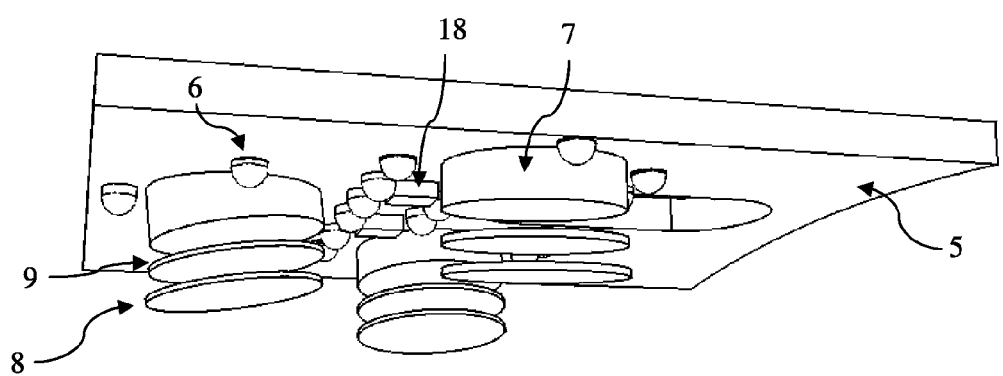

FIGS. 2A and 2B show an example of the components of the imaging system of the automated venipuncture device of the present invention. The imaging system shown in FIGS. 2A and 2B contains a plurality of highly diffuse infrared light emitting diodes (LEDs) 6 for illuminating the target vessel of a human, such as a vein. The imaging system further contains a plurality of light detectors 7 for capturing an image, e.g., video image, of the target veins based upon infrared light reflected from the vessel. When the target vessels are disposed below subcutaneous fat in body tissue, the vessels can be clearly seen in a video image produced by the imaging system.

The light emitting diodes 6 may be "potted" or surrounded on their sides by a substantially opaque material which minimizes diffusion of light from the side of the light emitting diode 6. For optimum illumination, each light emitting diode should be focused at a select angle to maximize the concentration of light source at a select location within the target vessel. The light emitting diodes may be at about a 15° to about 30° angle of dispersion for maximizing concentration of the light source at selected location within a target vessel. For example, a 15 degree angle of dispersion (or focus angle) may be utilized for effective illumination. In certain embodiments, a dispersion angle of 30 degrees may be suitable for effective illumination. Other angles of dispersion (or focus angles) may be acceptable as well. The relatively narrow focus angle is beneficial as more light is directed into the human's tissue around the target vessel for trans-illumination. Each of the light emitting diodes 6 can be secured to an imaging system housing plate 5. The imaging system housing plate 5 is preferably a printed circuit board with integrated contacts for connecting to a battery source.

The imaging system of the present invention may also contain on the imaging system housing plate 5 a position sensor 18, as seen in FIGS. 2A and 2B, for providing a measurement of distance from the light emitting diodes 6 and the needle 13 to the target veins. This will ensure exact distances are known at all times. The position sensor located 18 on the imaging system may utilize a laser based system to determine the distance between the device and the target vein. The position sensor 18, together with the computer program sends out a burst/ping of laser light and determines the time for the laser light to bounce back. This time is then correlated with a distance.

As further shown in FIGS. 2A and 2B, the imaging system may also contain a plurality of infrared filtered light detectors 7. FIG. 2B further shows each light detector 7 containing a filter 8 on the lens 9 of the light detector that will allow only those wavelengths in the infrared range to pass through and then be subsequently imaged. The imaging system of the present invention may utilize interchangeable lenses to vary the field of view of the light detectors 7. The filter 8 and lens 9 setup may be attached to an image acquisition assembly unit of the light detector 7, through an attachment to the light detector 7.

The lens 9 may be configured to further focus the light emitted from the light emitting diodes 6 as desired. Alternatively, the lens 9 may be a variable focusing lens that is extended or retracted relative to a cylindrical extension to vary the focus of the light emitting diodes 6.

In certain embodiments of the present invention, the light detectors 7 will also be capable of being fixed or mounted on a motorized platform to pivot, providing image acquisition from various angles.

Use of the light emitting diodes 6 as a light source minimizes the danger of burning patients with whom the automated venipuncture device is used and will prevent injury to the eyes of a clinician or the human if they inadvertently look directly into the light source. The lens 9 further shields the human from any heat which is produced by the light emitting diodes 6. As previously discussed, light emitting diodes 6 are available which emit in a relatively narrow spectral band, preferably with a predominant wavelength of about 700 nm to about 910 nm. Light with this wavelength has been found to highlight target vessels, e.g., veins, with respect to the tissue.

Based on the light reflected from the target vein, the light detector 7 generates an image, e.g., video image, of the target vein in the form of an electrical video signal. The enhanced video image signal is provided to a computer 1 through an interface cable 2, as shown in FIG. 1. The computer 1 captures still images from the image signal which may be saved in digital format on a digital storage device either in or connected to the computer 1. One skilled in the art would understand that various electronic storage devices, such as external hard drives and the like may be utilized in the present invention.

Figure 1A:
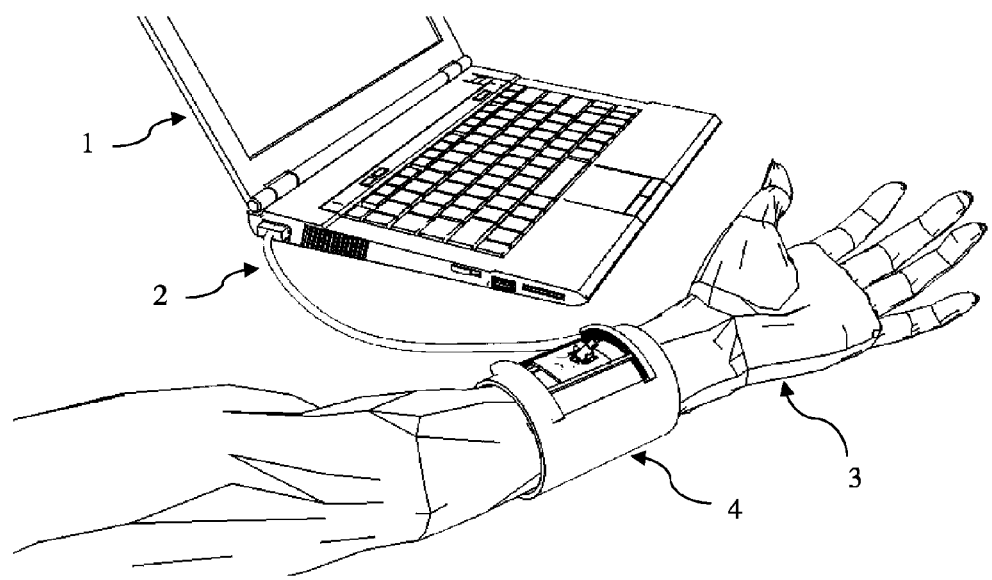
FIG. 1A shows a self-contained, automated venipuncture device of the present invention connected to a human, and hard wired to the computer (PC) interface component of the device.
Figure 1B:
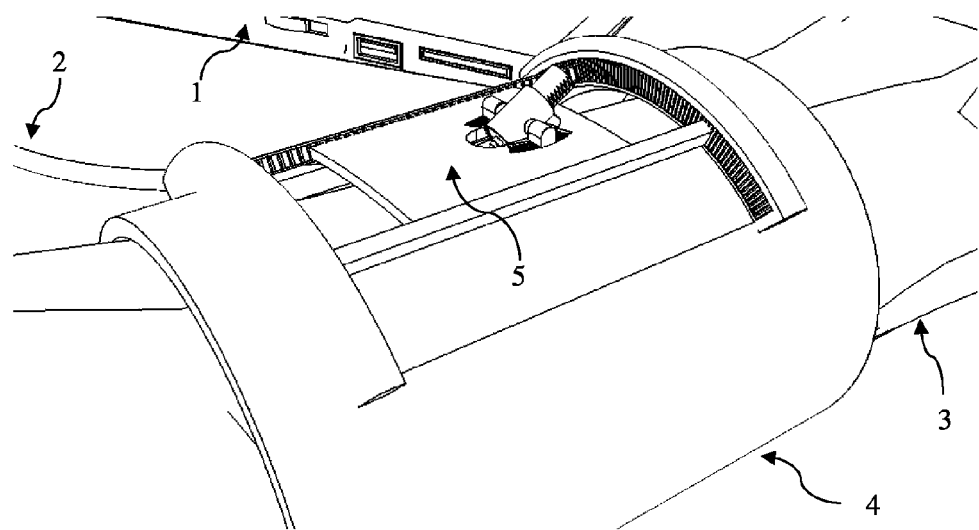
FIG. 1B is a close-up of a self-contained, automated venipuncture device of the present invention.

As shown in FIGS. 1A and 1B, a preferred embodiment of the present invention is contemplated wherein the imaging system housing plate 5 that houses the components of the imaging system is enclosed in a cuff-like structure 4. The present invention is not limited to this specific set-up and other means for securing the imaging system to the automated puncturing device are contemplated.

Automated Robotic End-Effector Unit

In preferred embodiments, another component of the automated venipuncture device of the present invention is an automated robotic end-effector unit that provides robotically controlled needle motion and which is capable of robotically guiding the needle into a target vessel designated by the computer or operator.

Figure 3A:
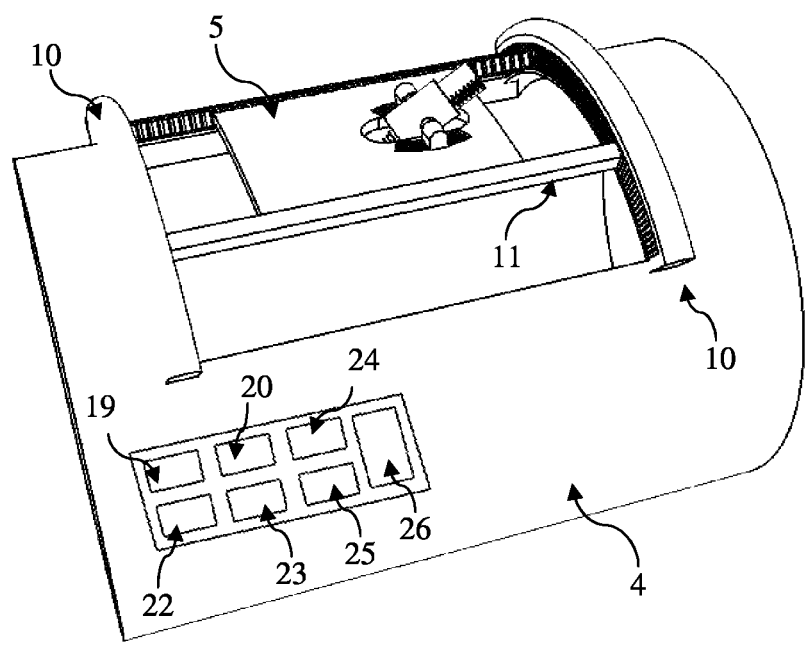
FIG. 3A is an illustration a cuff-like harness, automated robotic end-effector unit and imaging system.
Figure 3B:
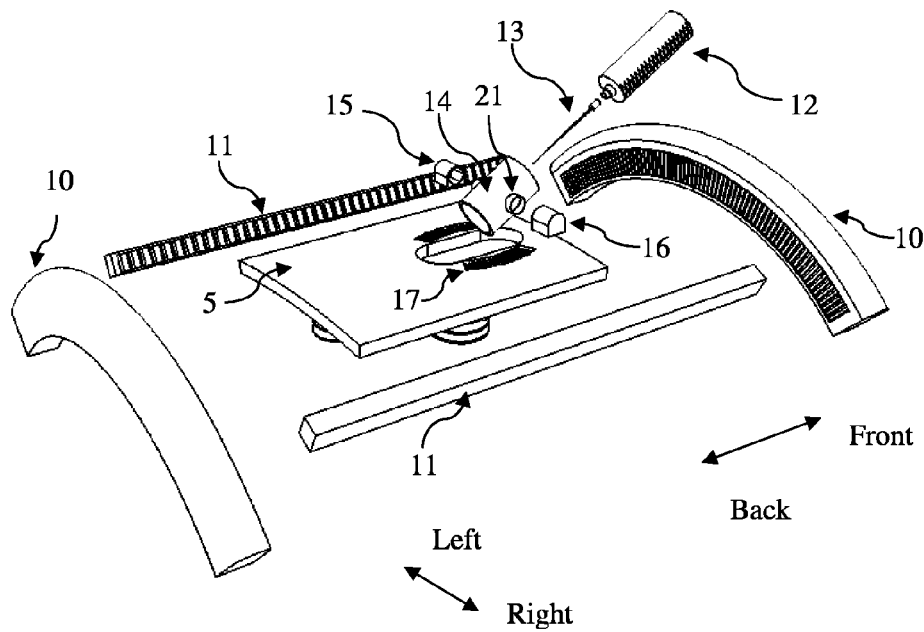
FIG. 3B is a blowout of an automated robotic end-effector "positioning" unit and its individual robotic components.
Figure 3C:
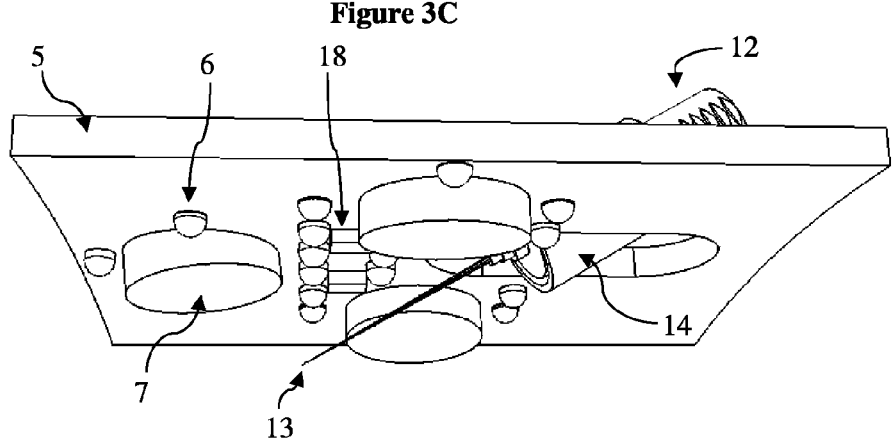
FIG. 3C illustrates an imaging system assembly in association with the robotically driven needle of the automated robotic end-effector unit.

A representative automated robotic end-effector unit of the automated venipuncture device of the present invention is shown in FIGS. 3A, 3B, and 3C.

The robotic automated end-effector unit may utilize, for example, a combination of a guidance system based on a derived three-dimensional (3D) coordinate map of the target vein, and a guidance system based on haptic or force feedback. Both systems standing alone have advantages and disadvantages, but if used in compliment provide an optimal system for robotic venipuncture. The haptic system alone is limited in the fact that it does not take into consideration the depth penetrated within the system, only the fact that the vein has been punctured. The 3D coordinate map based guidance system will validate that the needle is in the correct location, that it has entered the vessel, and that a certain penetration depth has not been exceeded This imaging system is only one level of safety protection. In order to ensure a robust safety mechanism for the device, both systems will be employed in tandem to ensure safety.

The three-dimensional (3D) imaging technology of the present invention can be used to automatically and accurately guide a needle to a location of the target vessel. Actual insertion of the needle into the skin and into a vessel is a dynamic process due to the elasticity of tissue. Stretching and deformation of the skin will result in effects not anticipated or compensated for by a system based on visualization alone. Therefore, haptic or force feedback is used to account for these effects.

Utilizing the automated venipuncture device of the present invention, when the needle is actually inserted into the skin, and punctures the target vessel wall, force and position profiles are generated that are sufficiently distinct to implement automatic needle withdrawal, preventing an overshoot of the needle.

The present invention therefore preferably utilizes both force and position profile technologies. By using the coordinates generated from the three-dimensional (3D) imaging system, a needle can be robotically guided to the target vessel, and when inserted into the vessel, force feedback prevents the needle from overshooting its target.

Figure 5:
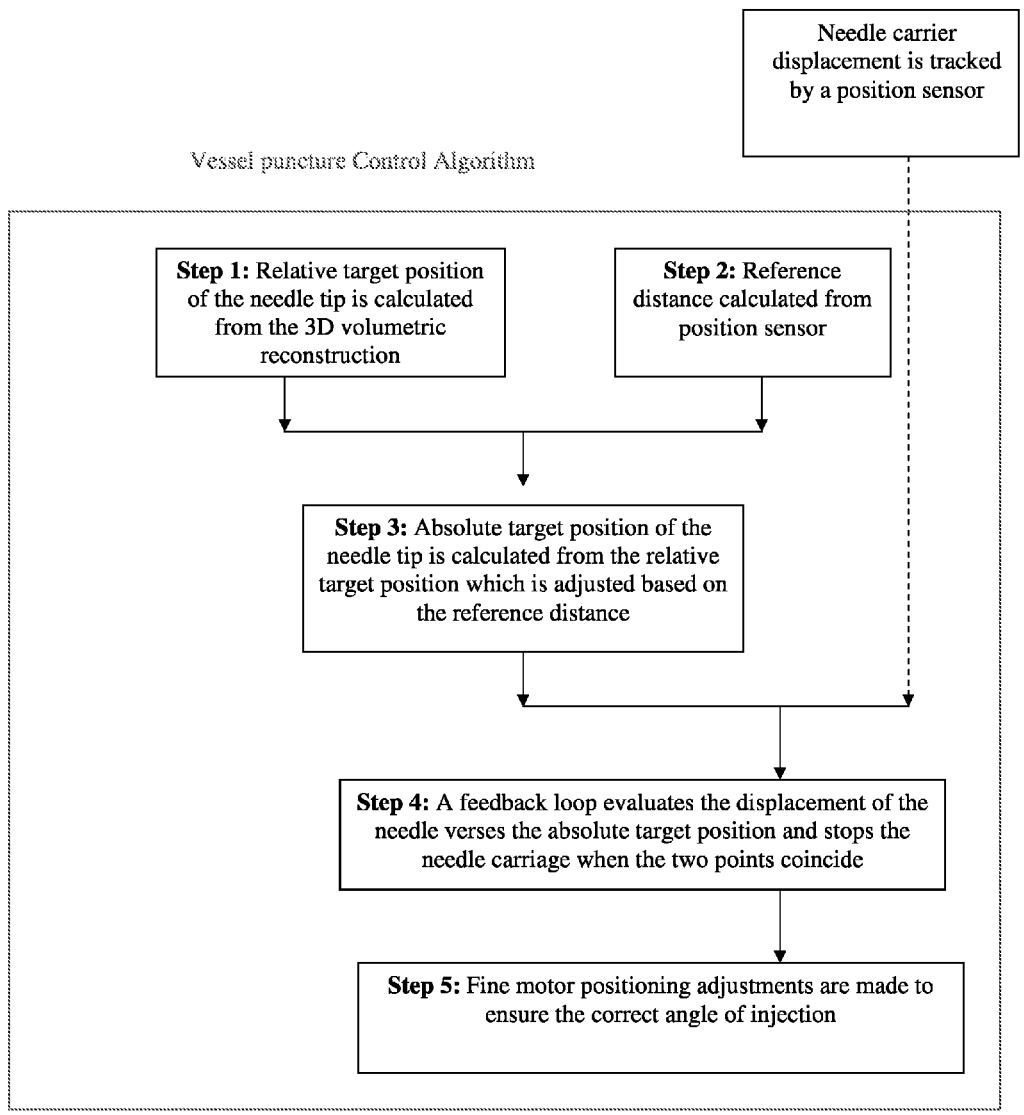
FIG. 5 is a flow diagram of a vessel puncture control algorithm and the methods for the control of the venipuncture device.

In certain embodiments of the present invention, one governing algorithm that may be utilized to control the position and injection of the needle 13 (FIGS. 3B, 3C) into the target vessel, is functionally diagrammed in FIG. 5. A first processor 19 (FIG. 3A) is provided for calculating a relative needle target puncture position using the 3D volumetric image provided by the image reconstruction program is first used to compute a relative target position for the needle (FIG. 5, Step 1). A position sensor 18 (FIGS. 2A, 2B, 3C) is provided for identifying the absolute distance description of a device reference point from the target vessel (FIG. 5, Step 2). A second processor 20 (FIG. 3A) is provided for calculating the absolute target spatial position for the needle by adjusting the relative target position from the first processor 19 by the absolute distance obtained from the position sensor 18 (FIG. 5, Step 3). A second position sensor 21 (FIG. 3B), within the device carrier housing 14 (FIG. 3B), is provided for identifying the current position description of the needle device carrier 12 (FIG. 3B). A third processor 22 (FIG. 3A) is provided for feedback control of the needle device carrier 12 with respect to the absolute target spatial position for the needle provided from the second processor 20. The third processor 22 stops the needle carrier 12 when the spatial position from the second position sensor 21 coincides with the absolute target spatial position for the needle provided from the second processor 20 (FIG. 5, Step 4). Finally up and down movement of the needle 13 is controlled by a fourth processor 23 (FIG. 3A), which adjusts the angle of the needle 13 through servo motor 16 (FIG. 3B) (FIG. 5, Step 5).

First processor 19, second processor 20, third processor 22, and fourth processor 23, are computational units which can be software or hardware modules arranged separately or in any appropriate combination as part of a computer 1. In addition these processors could also be subroutines within a piece of software contained in a computer 1.

The movement of the needle device carrier 12 is driven by a set of servo motors 15, 16, contained within the needle device carrier housing 14. Left to right coarse adjustment (shown by the arrow in FIG. 3B) is driven by servo motors within gear railing 10. Front to back movement (shown by the arrow in FIG. 3B) is driven by servo motors within the gear railing 11. Fine left to right movement is driven by servo motor 15. Fine up and down movement is driven by servo motor 16.

Injection of the needle 13 is driven by servo motors within the needle device carrier housing 14.

After the medical procedure of interest is completed, a signal from a fourth processor 23, will reverse the servo motor within 14, to withdraw the needle 13 from the target vessel, and subsequently return the needle device carrier 12 to the starting position.

Computer Component

The computer component of the present invention performs several discreet functions. These include (1) controlling the light source (e.g., LEDs)/light detector array (e.g., photodetectors); (2) creating a three-dimensional (3D) map of the target vessel position; (3) controlling the motion of the automated robotic end-effector unit; and (4) receiving feedback from the end-automated robotic end-effector unit for purposes of generating force and position profiles, and applying this feedback by adjusting the amount of force applied to the needle to penetrate the skin and vein of the human.

Any commonly available personal computer may be used for these purposes. The computer must have a physical interface to both the light source/light detector units and to the automated robotic end-effector unit. The computer must have the capability of turning on and off various light sources and reading the results from the light detectors. In addition, the computer must be capable of providing commands to the automated robotic end-effector unit and reading feedback signals from there. Additionally, the computer must be capable of generating the three-dimensional (3D) maps and the force and position profiles. One with skill in the art will realize that there are many ways of implementing software to perform these functions, and the actual arrangement and architecture of that software is not the subject of this invention.

In certain embodiments, the computer will utilize a software program for reconstructing a three-dimensional model from the images housed in a computer interface. The same software may also be utilized for evaluating the three-dimensional images and guiding the robotically driven needle.

In certain other embodiments, a small, special purpose ASIC (application-specific integrated circuit) may also be utilized in place of the computer and may be integrated into the device. Additionally, hardwire logic, gate array and state machine technologies can also be utilized in place of the computer.

The overall system must also include a mechanism for holding the human's body, e.g., limb, still and in place during the procedure, and there are several commercially-available mechanisms capable of performing this function.

Safety Feedback System

Figure 6:
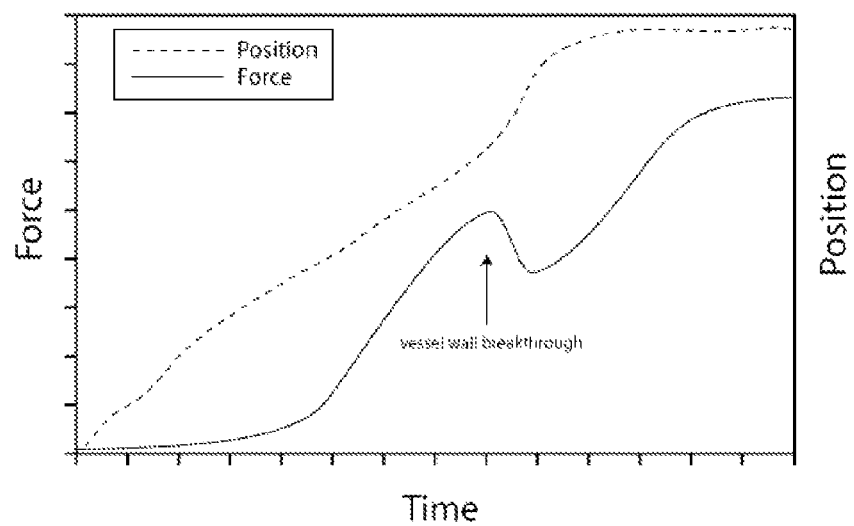
FIG. 6 shows an Example Decrease in force observed after needle has penetrated a target vein.

A pressure sensor coupled with the servo motor, both contained within the needle device carrier housing 14, responsible for needle injection transfers pressure readings to a first processor 24. The first processor 24 computes a change in applied force over time. A second processor 25, monitors the change in applied force over time and will switch off the servo motor, within the needle carrier housing 14, after an increase in pressure is observed, FIG. 6.

A secondary safety system is also included through the imaging system and 3D reconstruction algorithm. While venipuncture is taking place, the imaging system and reconstruction algorithm are working in real time and will determine the penetration depth of the needle 13 into the target vessel. A third processor 26, will integrate the penetration depth data with the pressure sensor data from the second processor 25 and will ensure that the servo motor, within the device housing 14, is switched off either after the aforementioned change in pressure is observed or the correct depth is penetrated.

Methods of Three-Dimensional Imaging

Another embodiment of the present invention is directed to methods of conducting fully automated venipuncture in a human. The method combines the automated venipuncture device of the present invention together with a novel near infrared imaging techniques to generate a three dimensional map of subcutaneous vessels in real time, allowing instant visualization of the vessels. Although the use of near infrared light has been used in the past to generate images of subcutaneous veins, they are two dimensional representations of the vessels. By combining multiple near infrared images of the vascular network via diffuse optical tomography (DOT), one can generate a three dimensional representation of the vessels. This will far exceed current techniques of 3D visualization in efficiency, time and cost. The resultant 3D representation of the vessel will subsequently be used to provide spatial position cues to an automated venipuncture device. The needle puncture system, in turn, will have an associated pressure feedback in order to assure the safety of the device.

Presently, diffusion optical tomography is a widely utilized optical image reconstruction tomographic technique. Examples of references which disclose this technique include: U.S. Pat. No. 5,813,988 to Alfano et al. entitled "Time-Resolved Diffusion Tomographic Imaging In Highly Scattering Turbid Media," which issued Sep. 29, 1998; W. Cai et al., "Time-Resolved Optical Diffusion Tomographic Image Reconstruction In Highly Scattering Turbid Media," Proc. Natl. Acad. Sci. USA, Vol. 93 13561-64 (1996); Arridge, "The Forward and Inverse Problems in Time Resolved Infra-red Imaging," Medical Optical Tomography: Functional Imaging and Monitoring SPIE Institutes, Vol. IS11, G. Muller ed., 31-64 (1993); and Singer et al., "Image Reconstruction of Interior of Bodies That Diffuse Radiation," Science, 248: 990-3 (1993), all of which are incorporated herein by reference.

The methods of the present invention allow for still images to be captured from the imaging system, and processed in order to generate a three-dimensional (3D) reconstruction of the target vessel. This process will be executed by a computer program contained within the computer 1.

Figure 4:
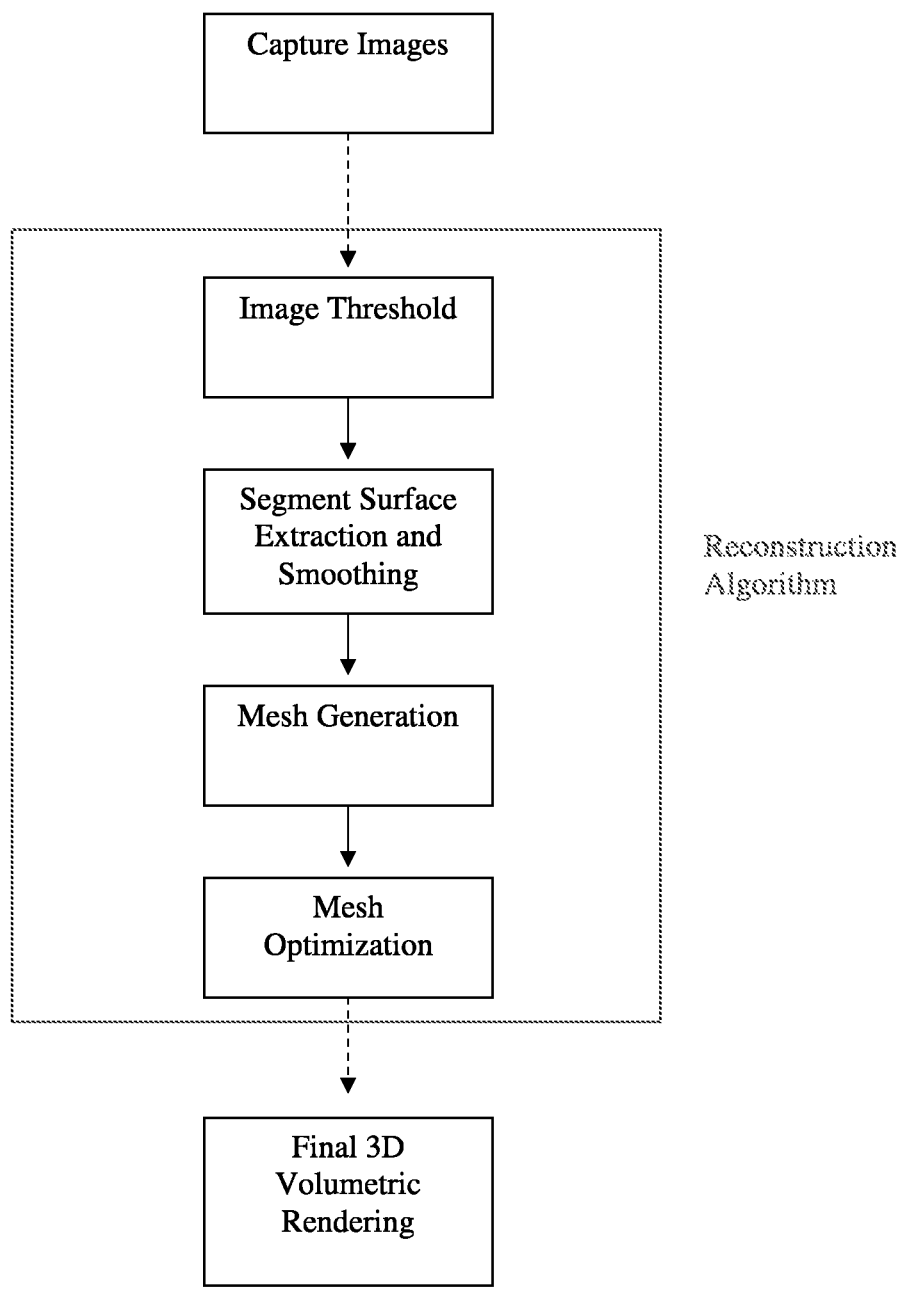
FIG. 4 is a flow diagram of computations made to reconstruct a three-dimensional (3D) representation of a vein from two-dimensional (2D) images.

The automated vessel puncture device of the present invention utilizes a computer program with real time image reconstruction using the principles of diffusion optical tomography and will compute the following sequential steps, as diagrammed in FIG. 4. 1) a thresholding process; 2) segment surface extraction and smoothing; 3) mesh generation based on advancing front algorithm or other methods; 4) mesh optimization.

Integration with Point of Care Analytical Applications

The present invention is also directed to integrating the automated vessel puncture device as a kit, or a modified device to include analytical assays. These point of care assays include, but are not limited to: 1) glucose monitoring; 2) determination of pregnancy/ovulation; 3) measurement of coagulation/PT; 4) fecal occult blood; 5) determination of drugs of abuse; 6) detection of H. pylori; 7) detection of HIV; 8) monitoring of cholesterol levels.

For these types of applications, blood can be withdrawn from a target vessel of a human utilizing the automated vessel puncture device of the present invention and then introduced into a point of care diagnostic assay.

DETAILED DESCRIPTION OF THE PREFERRED EMBODIMENTS

The present invention will further be appreciated with respect to the following non-limiting example.

Example 1

An Automated Venipuncture Device

An automated venipuncture device was built in three separate pieces: 1) a three-dimensional imaging system; 2) a needle carriage; and 3) a computer software that included both a three-dimensional (3D) reconstruction algorithm and a device control program.

The imaging system was setup as an off-board construction and was mounted to an off the shelf laboratory clamp stand. For the imaging system, 3 infrared filtered cameras (CCD cameras) were used, and a light source that had an infrared filter. The cameras were interfaced with a laptop computer using a RCA to USB adaptor and saved to a hard drive using SuperDVR image acquisition software.

A needle carriage was designed in Solidworks, and a prototype was constructed from a thermo responsive polymer using a rapid prototyping machine. Servo motors, pressure sensors, and distance determiners were then glued to the cured polymer pieces and the needle carriage was assembled on an arm cuff.

For the image reconstruction program various subroutines were combined together in Matlab, as individual m-files. The first sub routine read in the images and color thresholds them in order to refine the contrast and clarity of the image. The second sub routine segmented the images into regions of interest, and defined vessel boarders. The third subroutine generated a three dimensional finite element mesh that was an approximation of the vessel that was reconstructed. The fourth subroutine utilized the regions of interest and refined the three dimensional finite element mesh to yield the final three dimensional vessel reconstruction. This then provided relative spatial coordinates which were used in conjunction with a distance readout from a laser based device position sensor, that determined the absolute positioning of the vessel with respect to the venipuncture device. The imaging system resulted in the reconstruction of multiple vessels, that provided multiple targets to choose from. Using another Matlab subroutine, which provided a graphical user interface for the user, the user was able to choose the vessel that was punctured.

For the device control program, a pre-existing program utilizing the Visual C++ language was modified. Via a Labview A/D card in the computer, the routines generated in Visual C++ automatically controlled the movement of the needle carriage and monitored the distance displacement. A feedback loop was then used to monitor the displacement of the carriage relative to the injection point determined from the image reconstruction software.

The final portion of the prototype was an integrated image and pressure based safety feedback system. For this a pressure sensor was coupled to an injection servo to monitor the resistance during injection in real time. After a significant drop in force was observed (0.1-1.0 N), the system stopped the injection servo. The imaging system was concurrently working and measured the depth of injection of the needle into the vessel, and within a separate program (also written within Matlab) stopped the needle when it penetrated 30-60% into the overall thickness of the vessel.

The above example is merely demonstrative of an automated venipuncture device and one of ordinary skill in the art having the information contained in this specification will recognize obvious modifications which may be made.

What is claimed is:

1. A portable automated venipuncture device adapted for placement on an appendage of a human to draw blood from an optimal target vessel, comprising:
   i) a near infrared three-dimensional imaging system enclosed in a cuff-like structure for attachment to an appendage of a human and configured to a subcutaneous target vessel of a human for venipuncture comprising at least one near infrared light source for emitting infrared light and a plurality of light detectors for capturing reflected near infrared light from the target vessel and configured to generate still images of subcutaneous vessels of the human, wherein the device comprises a plurality of near infrared light sources which are light emitting diodes, and the light emitting diodes are at a 15° to a 30° angle of dispersion for maximizing concentration of the light source at selected location within a target vessel;
   ii) an automated robotic end-effector unit comprising a needle for target vessel puncture and blood acquisition, a pressure sensor configured to detect stretching and deformation of the skin and a needle guidance system that utilizes haptic and force feedback profiles for positioning the needle at the target vessel, adjusting the amount of force applied to the needle, and guiding the needle into the target vessel;
   iii) a computer connected to the near infrared light source and robotic end-effector unit, said computer configured to receive the still images from the imaging system and generate an image threshold using profiles of pixel intensity values of the still images and refine contrast and clarity of the still images, the computer further configured to utilize the image threshold to conduct segment surface extraction and smoothing to define borders and midline of subcutaneous vessels and conduct mesh generation to define and optimize a true three-dimensional geometry representing size, shape and volumetric reconstruction of the subcutaneous vessels; the computer further configured to calculate (a) a relative target position of the needle tip utilizing the three-dimensional volumetric reconstruction of subcutaneous vessels; (b) a reference distance of the needle tip utilizing a position sensor located on the imaging system; and (c) the absolute target position of the needle tip based on the relative target position of step (a) that is adjusted based on the reference distance of step (b) to provide haptic force and feedback profiles, the computer configured to send the haptic force and feedback profiles to the needle guidance system to position the needle track the displacement of the needle device carrier by the position sensor, and evaluate the displacement of the needle verses the absolute target position utilizing a feedback loop within the automated venipuncture device, wherein needle placement is stopped when the needle displacement and absolute target position coincide, thereby ensuring the correct angle of injection utilizing fine motor positioning adjustments, such that when the imaging system and the robotic end-effector unit are attached to an appendage of a human, the combined use of haptic, imaging and force feedback profiles generate a three-dimensional map of subcutaneous vessel and an optimal vessel is targeted for venipuncture and the needle is guided into the optimal target vessel for blood acquisition; and
   (iv) a point of care diagnostic assay means, the portable automated venipuncture device configured to introduce a blood sample obtained by the robotic end-effector unit into the point of care diagnostic means to provide one or more assays on the blood sample.

2. The portable automated venipuncture device of claim 1, wherein the near infrared light source has a frequency range from 700 nm to 910 nm.

3. The portable automated venipuncture device of claim 2, wherein the near infrared light source has a frequency range from 730 nm to 850 nm.

4. The portable automated venipuncture device of claim 2, wherein the near infrared light source is a light emitting diode.

5. The portable automated venipuncture device of claim 1, wherein the light detector is selected from the group consisting of photodetectors, and near infrared charged-coupled device (CCD) cameras.

6. The portable automated venipuncture device of claim 1, wherein the imaging system comprises an array of nine light emitting diodes and four photodetectors, wherein the array of light emitting diodes and photodetectors provides for sixteen light emitting diode/detector pairings, each corresponding to an orientation of a subcutaneous vessel of a human.

7. The portable automated venipuncture device of claim 6, wherein a raw measurement of the imaging system is calculated by the computer using Formula (I):

$$D=(f_{deoxy,1}-f_{oxy,1})-(f_{deoxy,2}-f_{oxy,2})$$

where 1 and 2 are two different light emitting diodes and D is a vector.

8. The portable automated venipuncture device of claim 7, wherein the computer is configured to use the raw measurement to reconstruct positioning and orientation of the automated robotic end-effector unit.

9. The portable automated venipuncture device of claim 1, wherein the light detector is configured to generate near infrared video images of the target vein based on the light reflected from the target vessel.

10. The portable automated venipuncture device of claim 9, wherein the video images are provided to the computer through an interface cable, and the computer is configured to capture still images of the target vein, the still images being stored in digital format on a digital storage device.

11. The portable automated venipuncture device of claim 10, wherein the digital storage device is connected to the computer.

12. The portable automated venipuncture device of claim 10, wherein the digital storage device is inside the computer.

13. The portable automated venipuncture device of claim 10, wherein the computer is configured to generate a three dimensional representation of the target vessel.

14. The portable automated venipuncture device of claim 1, wherein the device comprises a plurality of near infrared sources, the near infrared sources are light emitting diodes, and the light emitting diodes are at a 0° to 90° angle of dispersion for maximizing concentration of the light source at selected location within a target vessel.

15. The portable automated venipuncture device of claim 1, wherein the light source is secured to an imaging system housing plate, and the imaging system housing plate is a printed circuit board with integrated contacts for connecting to a battery source.

16. The portable automated venipuncture device of claim 15, wherein a position sensor for providing a measurement of the distance from the light source and needle to a target vessel is secured to the imaging system housing plate.

17. The automated venipuncture device of claim 1, wherein the light source and light detectors are fixed to a pivotable, motorized platform for providing image acquisition of target vessels from various angles.

18. The automated venepuncture device of claim 1, further comprising a position sensor, wherein the position sensor utilizes a laser based system to determine the distance between the device and the target vein.

19. The automated venipuncture device of claim 18, wherein the position sensor together with the computer program sends out a burst/ping of laser light and determines the time for the laser light to bounce back in order to correlate the time with a distance.

20. A portable automated venipuncture device adapted for placement on an appendage of a human to draw blood from an optimal target vessel, comprising:

i) a near infrared three-dimensional imaging system enclosed in a cuff-like structure for attachment to an appendage of a human and configured to a subcutaneous target vessel of a human for venipuncture comprising at least one near infrared light source for emitting infrared light and a plurality of light detectors for capturing reflected near infrared light from the target vessel and configured to generate still images of subcutaneous vessels of the human;

ii) an automated robotic end-effector unit comprising a needle for target vessel puncture and blood acquisition, a pressure sensor configured to detect stretching and deformation of the skin and a needle guidance system that utilizes haptic and force feedback profiles for positioning the needle at the target vessel, adjusting the amount of force applied to the needle, and guiding the needle into the target vessel;

iii) a computer connected to the near infrared light source and robotic end-effector unit, said computer configured to receive the still images from the imaging system and generate an image threshold using profiles of pixel intensity values of the still images and refine contrast and clarity of the still images, the computer further configured to utilize the image threshold to conduct segment surface extraction and smoothing to define borders and midline of subcutaneous vessels and conduct mesh generation to define and optimize a true three-dimensional geometry representing size, shape and volumetric reconstruction of the subcutaneous vessels; the computer further configured to calculate (a) a relative target position of the needle tip utilizing the three-dimensional volumetric reconstruction of subcutaneous vessels; (b) a reference distance of the needle tip utilizing a position sensor located on the imaging system; and (c) the absolute target position of the needle tip based on the relative target position of step (a) that is adjusted based on the reference distance of step (b) to provide haptic force and feedback profiles, the computer configured to send the haptic force and feedback profiles to the needle guidance system to position the needle track the displacement of the needle device carrier by the position sensor, and evaluate the displacement of the needle verses the absolute target position utilizing a feedback loop within the automated venipuncture device, wherein needle placement is stopped when the needle displacement and absolute target position coincide, thereby ensuring the correct angle of injection utilizing fine motor positioning adjustments, such that when the imaging system and the robotic end-effector unit are attached to an appendage of a human, the combined use of haptic, imaging and force feedback profiles generate a three-dimensional map of subcutaneous vessel and an optimal vessel is targeted for venipuncture and the needle is guided into the optimal target vessel for blood acquisition;

(iv) a position sensor, wherein the position sensor utilizes a laser based system to determine the distance between the device and the target vein, the position sensor together with the computer program sends out a burst/ping of laser light and determines the time for the laser light to bounce back in order to correlate the time with a distance; and (v) a point of care diagnostic assay means, the portable automated venipuncture device configured to introduce a blood sample obtained by the robotic end-effector unit into the point of care diagnostic means to provide one or more assays on the blood sample.

\* \* \* \* \*